United States Patent [19]

Zupancic

[11] 4,201,870
[45] May 6, 1980

[54] PROCESS FOR THE PREPARATION OF 2-(3-BENZOYLPHENYL)-PROPIONIC ACID

[75] Inventor: Boris Zupančič, Ljubljana, Yugoslavia

[73] Assignee: LEK Tovarna Farmacevtskih in Kemicnih Izdelkov, n.sol.o., Ljubljana, Yugoslavia

[21] Appl. No.: 842,824

[22] Filed: Oct. 17, 1977

[30] Foreign Application Priority Data

Oct. 18, 1976 [YU] Yugoslavia ........................ 2548/76

[51] Int. Cl.$^2$ ...................... C07C 69/76; C07C 65/20
[52] U.S. Cl. ...................................... 562/460; 560/52
[58] Field of Search ........................... 560/52; 562/460

[56] References Cited

U.S. PATENT DOCUMENTS

| 3,828,093 | 8/1974 | Bays | 560/52 |
| 4,028,404 | 6/1977 | Bays | 560/52 |

*Primary Examiner*—Paul J. Killos
*Attorney, Agent, or Firm*—Pollock, Vande Sande and Priddy

[57] ABSTRACT

A process for the preparation of 2-(3-benzoylphenyl)-propionic acid or salt thereof wherein 3-benzoylphenyl acetonitrile or an alkoxide thereof is reacted with a methylating agent and wherein the mixture obtained is hydrolized to thereby provide the desired acid.

10 Claims, No Drawings

PROCESS FOR THE PREPARATION OF 2-(3-BENZOYLPHENYL)-PROPIONIC ACID

The present invention relates to a new process for the preparation of 2-(3-benzoylphenyl)-propionic acid of the formula

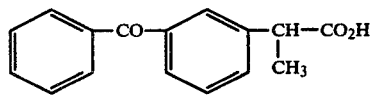
(VIII)

a compound possessing a significant antiinflammatory activity.

Hitherto there have been known two ways of preparing the aforesaid substance. According to the French Pat. No. 1,546,478, the starting substance may be 3-methylbenzoic acid yielding after three steps the 3-benzoylphenyl acetonitrile, which is converted into 3-benzoylphenyl-cyanoethyl acetate, whereupon the carbanion of the latter is methylated into the methyl-3-benzoylphenyl-cyanoethyl acetate and finally the end product is isolated by means of decarboxylation and saponification.

The last three steps of the cited patent are represented by the following scheme 1:

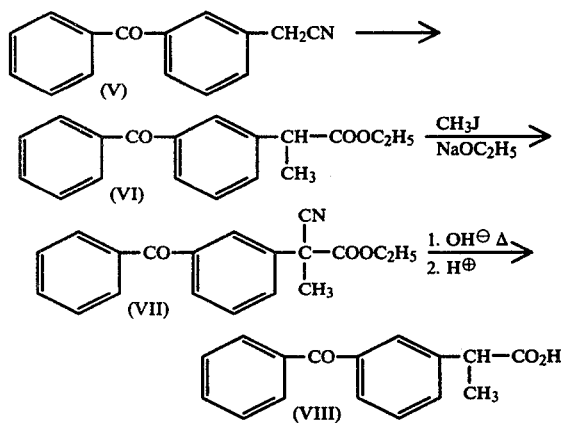

They do not comply with the notion of an easy technological performance in several points, to mention only the formation of the 3-benzoylphenyl-cyanoethyl acetate carbanion in absolute alcohol by means of sodium ethoxide. On the whole, said method is rather time-consuming, the yields of single reaction steps are not exactly satisfactory and the purification and isolation procedures of the intermediates are inconvenient. Owing to the numerous and complicated operations, it could not be considered as an optimum access to the 2-(3-benzoylphenyl)-propionic acid.

The second method according to the French Pat. No. 2,163,875 is certainly easier in this respect, as the single operations are not so numerous and exactiong. The desired compound may be obtained starting from 2-(3-carboxyphenyl)-propionitrile, converting by means of chlorination into the acid chloride, according to Friedel-Crafts into 2-(3-benzoylphenyl)-propionitrile and by means of hydrolysis into the 2-(3-benzoylphenyl)-propionic acid, as it is evident from the following scheme 2:

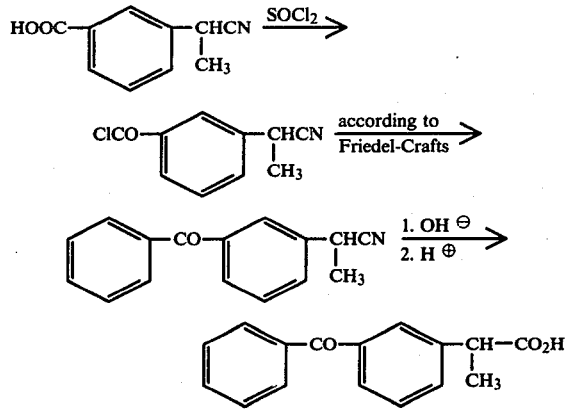

None of the cited reaction steps gives rise to any difficulties, yet the starting material, i.e. the 2-(3-carboxyphenyl)-propionitrile, is difficult to provide.

The synthesis thereof (E. R. Biehl, Hsueh-Ming Li, J. Org. Chem. 31, 602 (1965)) is not feasible at will even on laboratory scale. Even a slight excess of the weighed sample over the value given by the author results in resinification and impairs the yield as well as the purity. The working in liquid ammonia at −40° C. and the charging with metallic sodium under formation of sodium amide require a large capacity of the cooling plant, therefore relatively high investments and a certain minimum production to be profitable.

There has now been found a new, shorter and less exacting method for the preparation of 2-(3-benzoylphenyl)-propionic acid, wherein 3-benzoylphenylacetonitrile (V) or an alkoxide thereof comprising 1 to 4 carbon atoms in the alkoxy moiety are used as starting substances. The inventive starting substances are easily available.

The process according to the present invention is characterized is that a compound of the formula (V) or an alkoxide thereof comprising 1 to 4 carbon atoms in the alkoxy moiety is directly methylated whereupon the resulting methyl derivatives are hydrolyzed.

The methylation is performed in the presence of a catalyst, under conditions corresponding to the so-called Phase Transfer Catalysis (Norio Sugimoto et al, Chem. Pharm. Bull. 10, 427 (1962); M. Makosza, B. Serafimova, Roczniki chemii ann. soc. chim. Polonorum, 39, 1401 (1965); A. Brändström, U. Junggren, Tetrahedron Letters, 473 (1972); Charles M. Starks, Donald R. Napier, British Pat. No. 1,227,144 (7th April 1971); Eckehard V. Demlow, Angew. Chem. 86, 187 (1974); Jozef Dockx, Synthesis, 8, 441 (1973)).

The resulting 2-(3-benzoylphenyl)-propionitrile or the 2-(3-benzoylphenyl)-alkylester of propionic acid are subsequently hydrolyzed.

The methylation may be successfully conducted in a non-exacting manner in the presence of an ammonium quaternary compound in a two-phase system according to scheme 3:

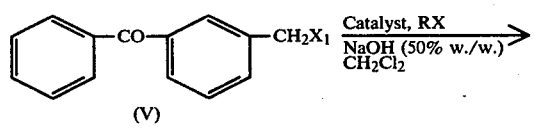

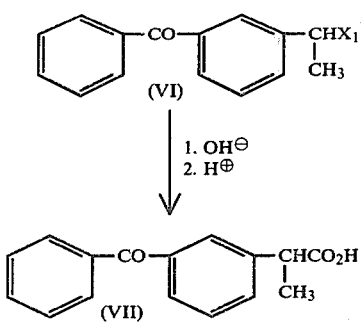

(VI)

1. OH⊖
2. H⊕

RX = CH₃J, CH₃Br, CH₃Cl, (CH₃)₂SO₄
X₁ = —CN, —CO₂R₁
R₁ = lower alkyl

As quaternary ammonium compounds there should be cited e.g. benzyltriethyl ammonium chloride, tetrabutyl ammonium hydrogensulfate and tricaprilylmethyl ammonium chloride.

The reaction is performed at a gradually increasing temperature within the range of $-5°$ to $+30°$ C.

By a selective conduction of the thermodynamically controlled reaction and a suitable choice of the reactants, mono- or dimethylation can be achieved in a yield exceeding 95%.

The resulting mono- or dimethylated product is subsequently subjected to acid or alkali hydrolysis and optionally the resulting 2-(3-benzoylphenyl)-propionic acid is converted into a metal salt or an addition salt of a nitrogen-containing base.

The purification is performed in a conventional manner, e.g. by means of chromatography, fractional precipitation, fractional distillation of the intermediates, and in the final step by means of crystallization from acetonitrile or a petrolether/benzene or acetone/water mixture.

EXAMPLE 1

Methylation of 3-cyanomethyl benzophenone

In a four-necked reaction flask of 250 ml., equipped with a stirred, thermometer and reflux condensor, at a temperature of not above 10° C. and under stirring there are dissolved 17.64 g. of redistilled 3-cyanomethyl benzophenone (fraction 185° to 220° C./0.5 mm. Hg, gas chromatography 97%) in 80 ml. of dichloromethane, subsequently there are added 48 ml. of 50% w./w. NaOH and finally 0.4 g. of benzyltriethyl ammonium chloride.

The temperature is then reduced to 5° C. and under moderate stirring (30 to 60 rpm) there is added dropwise a solution of 7.6 ml. of dimethylsulfoxide in 40 ml. of dichloromethane within 10 minutes. Subsequently the temperature is reduced to 3° C. and the stirring is continued for 140 minutes at the same rate. After altogether 150 minutes of reacting, the stirring is highly accelerated, the temperature is increased to 10° to 15° C. and there is added a solution of 1.8 ml. of dimethylsulfoxide in 8 ml. of dichloromethane. After stirring for 30 minutes at 10° to 15° C., the temperature is increased to 20° C. to 25° C., whereupon the stirring is continued for an additional hour at this temperature. The complete reaction lasts 240 minutes and is controlled by means of thin-layer chromatography (system: diisopropylether/conc. acetic acid 9:1).

The reaction mixture is poured into 100 ml. of water and the layers are separated. The aqueous layer is extracted by two 20 ml.-portions of dichloromethane and the resulting extracts are evaporated to dryness in a rotation evaporator. Yield: 21.7 g. of the crude product. After dissolving in 20 ml. of methanol there are added 0.96 g. NaOH (in rotulis) and under stirring 2.45 ml. (2.56 g.) of benzaldehyde. It is stirred overnight in a rotation evaporator. The following day 40 ml. of water are added and the mixture is extracted with four 40 ml.-portions of ether. The combined ethereal extracts are shaken with three 20 ml.-portions of a saturated $NaHSO_3$ solution, separated and dried over anhydrous $K_2CO_3$. Thereupon a filtration is performed and the ether is evaporated. The yield of the purified product: 18.4 g. (98.1%). Analysis by means of gas chromatography: 99.3%. The product is distilled at 179° to 210° C./0.3 mm. Hg. Two charges are distilled together and there are obtained 25.8 g. of the distillate (68.7% distillation yield or 67.5% theor.). The resulting product in the form of a light yellow oil is dissolved in 56.7 ml. of diisopropylether (2.2 ml./1 g.), refluxed for 30 minutes under the addition of 1% of active carbon (per total weight) and filtered hot through a folded filter. After cooling to ambient temperature, the product is transferred into a freezer for 24 hours and optionally inoculated with some seed crystals of 2-(3-benzoylphenyl)-propionitrile. The separating crystals are isolated on a pre-cooled suction filter and dried in vacuo. Yield: 15.5 g. (41.1% theor.) of 2-(3-benzoylphenyl)-propionitrile with a m.p. of 51.5° to 53.5° C. (Kofler). The literature cited on p. 3 discloses a m.p. of 54° C.

Hydrolysis of 2-(3-benzoylphenyl)-propionitrile into 2-(3-benzoylphenyl)-propionic acid 10.2 g. of 2-(3-benzoylphenyl)-propionitrile, recrystallized from diisopropylether, are dissolved in 85 ml. of methanol and water (1:1) and under stirring there are added 2.5 g. of KOH. It is refluxed for 24 hours (T—75° C.), cooled and evaporated to dryness. The oily residue is diluted with 63 ml. of water and extracted with four 27.0 ml.-portions of ether (after evaporation the ethereal layer contains 3.2 g. of the oily residue). The aqueous layer is stirred for 15 minutes with 0.54 g. of active carbon, filtered and the filtrate is cooled; 100 ml. of ether are added and the mixture is precipitated under stirring in the presence of some ice lumps by means of 5% w./w. HCl (49.5 ml.). After the separation of the layers, the ethereal layer is dried over $Na_2SO_4$, the drying agent is separated and the ether is evaporated. The residue consists of 7.2 g. of oil (65.2%), to which there are added 10.8 ml. of acetonitrile (1.5 ml./1 g.) and a spatula tip of active carbon. After 15 minutes of refluxing, it is filtered hot over a heated filter. The product is left to cool down to ambient temperature, whereupon it is kept overnight in a freezer (—15° C.). Then it is filtered over a pre-cooled suction filter, sharply aspirated and washed with three 5 ml.-portions of cool ether. It is dried in vacuo over $CaCl_2$ at 40° C. The yield amounts to 4.2 g. (58.4% theor.) of 2-(3-benzoylphenyl)-propionic acid with a m.p. of 92.5° to 94° C. (Kofler).

EXAMPLE 2

Methylation of 3-benzoylphenylacetonitrile

The procedure is the same as disclosed in the above Example 1 except that tetrabutyl ammonium hydrogensulfate (0.68 g.) is used as catalyst.

Owing to the slower reaction the reaction time is increased for additional 120 minutes (total duration of the reaction is 360 minutes) and the reaction temperature is raised to 25° to 30° C. after 240 minutes. There are obtained 18.4 g. (98.1%) of the crude product, which, after purification with benzaldehyde, yields 17.5 g. (93.5% theor.) of the purified product.

The distillation of two charges (35.0 g.) at 180° to 220° C./0.3 mm. Hg yields 24.1 g. (68.7%) of oil.

HYDROLYSIS 12.35 g. of redistilled 2-(3-benzoylphenyl)-propionitrile are dissolved in 19.1 ml. of methanol and, under stirring, there is added a solution of 5.1 g. KOH in 19 ml. of water and the mixture is refluxed for 24 hours. After the evaporation of the solvent, it is diluted with 78 ml. of water and extracted with four 35 ml.-portions of ether. The aqueous layer is stirred for 15 minutes with 1.3 g. of Calflo C®, produced by Johns-Mansville International Co., New York, USA, filtered and further purified by means of stirring with 0.65 g. of active carbon at 40° C. for 15 minutes. When the carbon is filtered off, the filtrate is evaporated on a rotation evaporator, cooled and precipitated with 5% w./w. HCl until the pH value of 1 is attained, which requires 50 ml. of the acid. Initially the product precipitates in flakes, subsequently it turns into a resinous lump, which is dissolved in 30 ml. of ether. The ethereal layer is separated off, whereas the aqueous layer is shaken with an equal quantity of ether. The combined ethereal layers are dried over $Na_2SO_4$ and finally ether is evaporated. The resulting yellow oil weighs 6.9 g. (50.6% theor.) and is dissolved in 34.5 ml. of ether, whereupon a solution of 5.4 ml. of dicyclohexylamine in 10 ml. of ether is added drop by drop under stirring at ambient temperature. After the dropwise addition of said solution, it is stirred on for further 30 minutes under ice-cooling. There results a white precipitate, which is filtered off and dried in vacuo at 40° C. over $CaCl_2$. There are obtained 10.0 g. (84.5% theor.) of a dicyclohexylamine salt of 2-(3-benzoylphenyl)-propionic acid, m.p. 144° to 146° C. (Kofler).

EXAMPLE 3

51.0 g. of 2-(3-benzoylphenyl)-propionitrile, obtained as disclosed in Example 2 and purified by means of benzaldehyde, are distilled in nitrogen atmosphere. At a temperature between 177° and 210° C./0.6 mm Hg there are distilled over 32.4 g. (63.6%) of the product. 31.85 g. of the distillate are dissolved in 266 ml. of a methanol/-water mixture (1:1) and 7.96 g. of KOH are added. Under stirring the mixture is refluxed for 24 hours, the solvent is evaporated, the residue diluted with 200 ml. of water and extracted by means of four 83.5 ml.-portions of ether. To the aqueous layer there are added 3.4 g. of Calflo C® and it is stirred for further 15 minutes. After the Calflo C® is separated off, it is stirred for further 15 minutes at 40° C. with 1.7 g. of active carbon. When the carbon is filtered off, the filtrate is cooled and it is precipitated with 85.5 ml. of 5% w./w. HCl in the presence of 100 ml. of ether under stirring. After the separation of the layers, drying over $Na_2SO_4$ and evaporation of ether on a rotation evaporator, there are obtained 15.1 g. (44%) of a light yellow oil, which is dissolved in 75.5 ml. of ether, whereupon a solution of 11.8 ml. of dicyclohexylamine in 25.0 ml. of ether is added under stirring at ambient temperature. After stirring for 30 minutes on ice, the separated salt is filtered off and dried. The yield is 23.2 g. of (89.3%) of a snow white product, m.p. 145° to 146° C. (Kofler).

The salt is dissolved in 80.9 ml. of ethylacetate and there are added 35.1 ml. of 2 N HCl under stirring and cooling. After the addition of the acid, the stirring is continued for further 10 minutes, whereupon the resulting hydrochloride is separated on a suction filter. The filter cake is washed with 30 ml. of ethylacetate and the filtrate is separated in a separating funnel into an aqueous and an organic layer. The latter is washed with water and dried over $Na_2SO_4$. The $Na_2SO_4$ is filtered off and the solvent is distilled over in a rotation evaporator (in vacuo up to 70° C.), whereupon there are obtained 13.1 g. (97.3%) of a light yellow oil, which is recrystallized from 19.65 ml. of acetonitrile under addition of 0.3 g. of active carbon. It is left overnight in a freezer, whereupon a snow white product is crystallized, which is washed twice on a suction filter with 6 ml.-portions of cool med. petrol (b.p. 60° C.).

Yield: 9.8 g. (74.7%) of 2-(3-benzoylphenyl)-propionic acid, m.p. 94.0° to 95.5° C.

What is claimed is:

1. A process for the preparation of 2-(3-benzoylphenyl)-propionic acid or salt thereof, characterized in that 3-benzoylphenyl acetonitrile or an alkoxide thereof comprising 1 to 4 carbon atoms in the alkoxy moiety is reacted with a methylating agent in a two-phase system, at a gradually increasing temperature within the range of −5° to +30° C. and in the presence of a quaternary ammonium compound, whereupon the mixture is hydrolized to thereby provide said acid.

2. A process as claimed in claim 1, characterized in that as methylating agent there is used methyl iodide, methyl bromide, methyl chloride, and dimethyl sulfate.

3. A process as claimed in claim 1, characterized in that as ammonium quaternary compound there is used preferably benzyltriethyl ammonium chloride, tetrabutyl ammonium hydrogensulfate, and tricaprilylmethyl ammonium chloride.

4. The process of claim 1 wherein said acid is converted into a metal salt or an addition salt of a nitrogen-containing base.

5. The process of claim 2 wherein said acid is converted into a metal salt or an addition salt of a nitrogen-containing base.

6. The process of claim 3 wherein said acid is converted into a metal salt or an addition salt of a nitrogen-containing base.

7. The process of claim 1 wherein the methylating is carried out in the presence of water.

8. The process of claim 1 wherein the methylating agent is selected from the group of methyl iodide, methyl bromide, methyl chloride, and dimethyl sulfate; said ammonium quaternary compound is selected from the group of benzyl triethyl ammonium chloride, tetrabutyl ammonium hydrogen sulfate and tricaprilyl methyl ammonium chloride.

9. The process of claim 8 wherein said acid is converted into a metal salt or an addition salt of a nitrogen-containing base.

10. The process of claim 1 which further comprises purifying said acid or salt thereof.

* * * * *